United States Patent
Smith, Jr.

(10) Patent No.: US 6,852,902 B2
(45) Date of Patent: Feb. 8, 2005

(54) METHOD OF REMOVING ENTRAINED SULFURIC ACID FROM ALKYLATE

(75) Inventor: Lawrence A. Smith, Jr., Pasadena, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 319 days.

(21) Appl. No.: 10/269,261

(22) Filed: Oct. 11, 2002

(65) Prior Publication Data

US 2004/0059172 A1 Mar. 25, 2004

Related U.S. Application Data

(60) Provisional application No. 60/364,884, filed on Mar. 15, 2002.

(51) Int. Cl.[7] .............................. C07C 2/62; C07C 7/144
(52) U.S. Cl. ......................... 585/718; 585/731; 585/818
(58) Field of Search ................................ 585/718, 731, 585/818

(56) References Cited

U.S. PATENT DOCUMENTS

| | | | |
|---|---|---|---|
| 2,091,917 A | 8/1937 | Fenske et al. ................. 196/46 |
| 2,472,578 A | 6/1949 | Ferris et al. ................... 196/13 |
| 3,013,093 A | * 12/1961 | Stiles .......................... 585/718 |
| 3,496,996 A | 2/1970 | Osdor ......................... 165/111 |
| 3,759,318 A | 9/1973 | Putney et al. ................ 165/108 |
| 3,839,487 A | 10/1974 | Clonts .................... 260/683.48 |
| 4,075,258 A | 2/1978 | Caulk et al. ............ 260/683.44 |
| 5,220,095 A | 6/1993 | Hommeltoft et al. ........ 585/720 |
| 5,420,093 A | 5/1995 | Joly et al. .................... 502/216 |
| 5,444,175 A | 8/1995 | Joly et al. .................... 585/714 |
| 5,785,933 A | 7/1998 | Cunningham et al. ...... 422/224 |

* cited by examiner

Primary Examiner—Thuan Dinh Dang
(74) Attorney, Agent, or Firm—Kenneth H. Johnson

(57) ABSTRACT

An improvement in the alkylation of olefins with isoalkanes in the presence of sulfuric acid wherein the sulfuric acid is removed from the product by a mechanical coalescer means prior to fractionation. No water wash or caustic treatment is required. Any sulfonates or sulfonic esters are removed by hydrodesulfurization or decomposition catalyst in a separate reactor or in either the deisobutanizer (DIB) or debutanizer (DB) column.

6 Claims, 3 Drawing Sheets

METHOD OF REMOVING ENTRAINED SULFURIC ACID FROM ALKYLATE

This application claims the benefit of provisional application Ser. No. 60/364,884 filed Mar. 15, 2002.

BACKGROUND OF THE INVENTION

1. Field of the Invention

The present invention relates to the treatment of alkylate product from a process wherein normal olefins are reacted with isoalkanes in the presence of sulfuric acid to produce alkylate product. More particularly the invention relates to a process wherein the effluent from the alkylation reactor is passed through a deentrainment device to remove sulfuric acid by coalescence and subsequently treated to remove sulfonates and sulfonic esters.

2. Related Information

In the petroleum refining industry, acid catalyzed alkylation of aliphatic hydrocarbons with olefinic hydrocarbons is a well known process. Alkylation is the reaction of a paraffin, usually isoparaffins, with an olefin in the presence of a strong acid which produces paraffins, e.g., of higher octane number than the starting materials and which boil in range of gasolines. In petroleum refining the reaction is generally the reaction of a $C_2$ to $C_5$ olefin with isobutane.

In refining alkylations, hydrofluoric or sulfuric acid catalysts are most widely used under low temperature conditions. Low temperature or cold acid processes are favored because side reactions are minimized. In the traditional process the reaction is carried out in a reactor where the hydrocarbon reactants are dispersed into a continuous acid phase.

Although this process has not been environmentally friendly and is hazardous to operate, no other process has been as efficient and it continues to be the major method of alkylation for octane enhancement throughout the world. In view of the fact that the cold acid process will continue to be the process of choice, various proposals have been made to improve and enhance the reaction and to some extent moderate the undesirable effects.

In the past the alkylate product has been washed with water or treated with caustic to remove or neutralize any carry over sulfuric acid. Both methods of treatment have drawbacks. When a water wash is used there is some carry over of water to the distillation columns used to separate the alkylate from unreacted materials. This water dilutes any acid left or dissolves any sulfonates or sulfonic esters which cause corrosion problems. The caustic tends to produce salts which can foul downstream heat exchangers, especially the reboiler in the recovery columns. Various solutions have been proposed for this problem. U.S. Pat. No. 5,220,095 disclosed the use of particulate polar contact material and fluorinated sulfuric acid for the alkylation.

U.S. Pat. Nos. 5,420,093 and 5,444,175 sought to combine the particulate contact material and the catalyst by impregnating a mineral or organic support particulate with sulfuric acid.

Various static systems have been proposed for contacting liquid/liquid reactants, for example U.S. Pat. Nos. 3,496,996; 3,839,487; 2,091,917; and 2,472,578. However, the most widely used method of mixing catalyst and reactants is the use of various arrangements of blades, paddles, impellers and the like that vigorously agitate and blend the components together, for example, see U.S. Pat. Nos. 3,759,318; 4,075,258 and 5,785,933.

It is an advantage of the present invention that it overcomes the water/sulfuric acid carryover by a more effective process of acid/water separation and recovery.

SUMMARY OF THE INVENTION

Briefly the invention comprises removing the sulfuric acid from the alkylate by mechanical means instead of water wash or caustic treatment product prior to separating the unreacted isobutane in a deisobutanizer (DIB) column, preferably to produce alkylate having a water content of less than 100 ppm. The preferred mechanical means comprises a vessel containing a coalescer material upon which the sulfuric acid impinges. The sulfuric acid, being much heavier than the hydrocarbon, falls out and may be removed by gravity. The alkylate product is then treated in a debutanizer (DB) column to simultaneously separate the normal butane from the product and remove sulfur contaminants such as sulfonates or sulfonic esters which are by-products from the alkylation. In a preferable embodiment the lower end, or stripping section, of the debutanizer (DB) is packed with a hydrodesulfurization catalyst which hydrogenates the sulfur compounds to hydrogen sulfide which can be removed with the butane overheads.

In another embodiment the hydrodesulfurization catalyst is placed in the stripping section of the deisobutanizer (DIB) column and the trace hydrogen sulfide is simply recycled back to the alkylation reactor which is capable of handling this corrosive material.

In another embodiment the effluent from the mechanical separation is fed to a standard down flow fixed bed reactor containing a hydrodesulfurization catalyst and the hydrogen sulfide produced is removed in the overheads from the deisobutanizer (DIB) column and recycled to the alkylation reactor.

Finally, in any of the above embodiments the hydrodesulfurization catalyst may be replaced with a decomposition type catalyst, such as palladium, to decompose the sulfonates and sulfonic esters to their constituent components.

DETAILED DESCRIPTION OF THE PREFERRED EMBODIMENT

The alkylate product to be treated may come from any cold acid alkylation process which uses sulfuric acid as the catalyst. Preferably, the fluid system comprises a liquid and is maintained at about its boiling point in the reaction zone.

Figure 1:
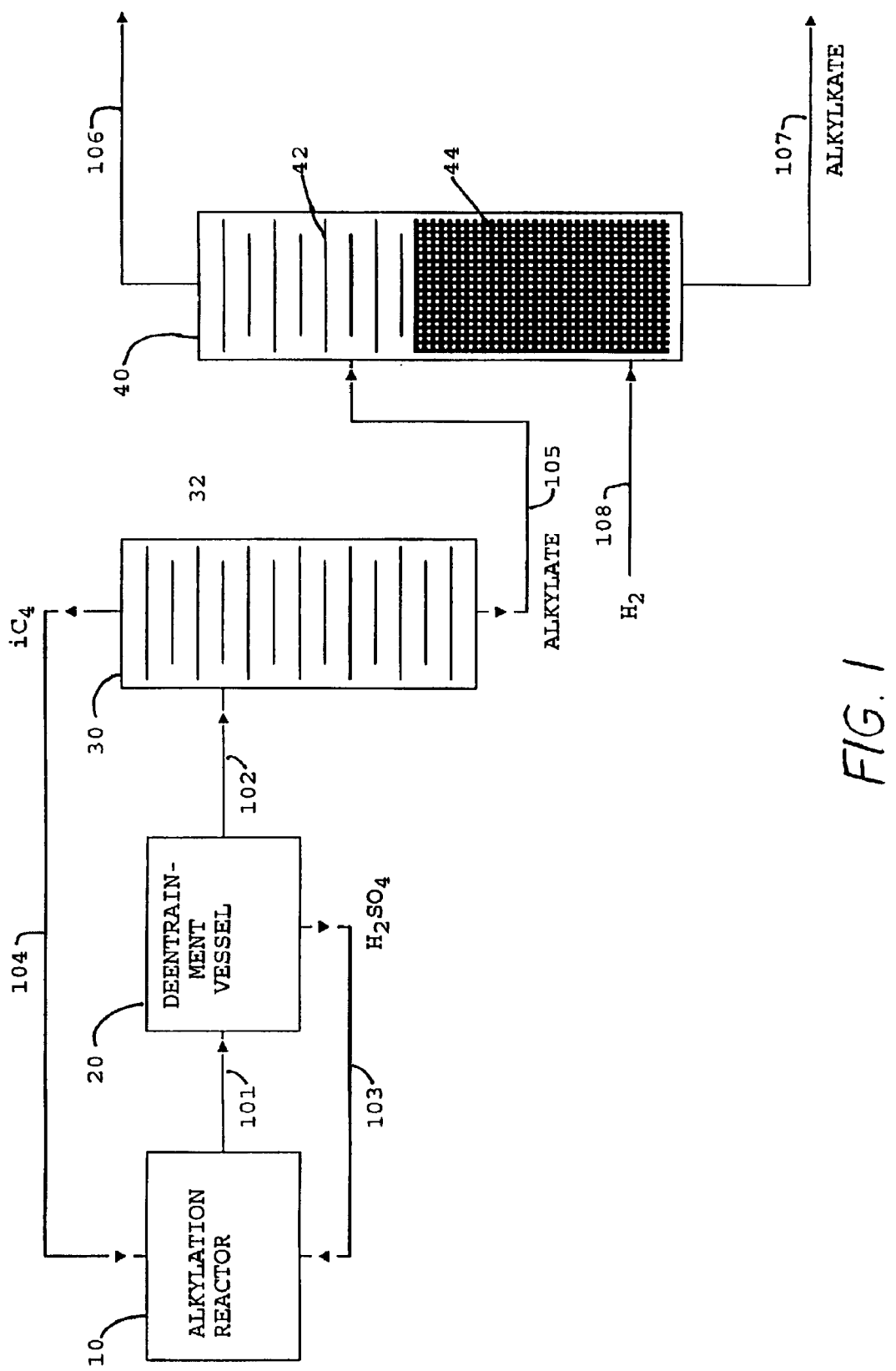
FIG. 1 is a simplified flow diagram in schematic form of one embodiment of the invention.

Typically the alkylate from the alkylation process contains some sulfuric acid as well as sulfonates and sulfonic esters which must be removed. Referring now to FIG. 1 a simplified flow diagram of one embodiment is shown. The alkylate is taken from alkylation reactor 10 via flow line 101 and fed to deentrainment vessel 20. Deentrainment vessel 20 contains a coalescer material upon which the sulfuric acid droplets impinge and fall out. The sulfuric acid and hydrocarbons in the alkylate product are practically insoluble in one another. The sulfuric acid droplets are collected and recycled to the alkylation reactor 10 via flow line 104. The coalescer comprises a conventional liquid-liquid coalescer of a type which is operative for coalescing vaporized liquids. These are commonly known as "mist eliminators" or "demisters". A suitable coalescer comprises a mesh such as a co-knit wire and fiberglass mesh. For example, it has been found that a 90 needle tubular co-knit mesh of wire and fiberglass such as manufactured by Amistco Separation Products, Inc of Alvin, Texas or ACS Industries LLC of Houston, Tex., can be effectively utilized, however, it will be understood that various other materials such as co-knit wire and teflon (Dupont TM), steel wool, polypropylene, PVDF, polyester or various other co-knit materials can also be effectively utilized in the apparatus. Various wire screen type packings may be employed where the screens are woven rather than knitted. Other acceptable coalescers include perforated sheets and expanded metals, open flow cross channel structures which are co-woven with fiberglass or other materials, such as polymers.

The liquid hydrocarbon material from the deentrainment vessel is passed to a deisobutanizer (DIB) column 30 via flow line 102 having distillation structure 32 where the isobutane is removed as overheads via flow line 104 and recycled to the alkylation reactor. The alkylate and normal butane are removed from the deisobutanizer (DIB) column 30 as bottoms via flow line 105 and fed to a debutanizer (DB) column 40 containing a bed 44 of hydrodesulfurization catalyst in the stripping section and standard distillation structure 42 in the remainder of the column. Hydrogen is fed via flow line 108. The sulfonates and sulfonic esters are converted to hydrogen sulfide by the catalyst which is removed in the overheads via flow line 106 along with the normal butane plus trace amounts of $H_2S$ or in the embodiment wherein the catalyst bed 44 contains a decomposition catalyst trace amounts of $SO_2$ and $SO_3$. The alkylate product is removed as bottoms via flow line 107.

Catalysts which are useful for the hydrodesulfurization reaction include Group VIII metals such as cobalt, nickel, palladium, alone or in combination with other metals such as molybdenum or tungsten on a suitable support which may be alumina, silica-alumina, titania-zirconia or the like. Normally the metals are provided as the oxides of the metals supported on extrudates or spheres and as such are not generally useful as distillation structures.

The catalysts may additionally contain components from Group V and VIB metals of the Periodic Table or mixtures thereof. The use of the distillation system reduces the deactivation and provides for longer runs than the fixed bed hydrogenation units of the prior art. The Group VIII metal provides increased overall average activity. Catalysts containing a Group VIB metal such as molybdenum and a Group VIII such as cobalt or nickel are preferred. Catalysts suitable for the hydrodesulfurization reaction include cobalt-molybdenum, nickel-molybdenum and nickel-tungsten. The metals are generally present as oxides supported on a neutral base such as alumina, silica-alumina or the like. The metals are reduced to the sulfide either in use or prior to use by exposure to sulfur compound containing streams.

The properties of a typical hydrodesulfurization catalyst are shown in Table I below.

TABLE I

| Manufacture | Criterion Catalyst Co. |
|---|---|
| Designation | C-448 |
| Form | Tri-lobe Extrudate |
| Nominal size | 1.2 mm diameter |
| Metal, Wt. % | |
| Cobalt | 2–5% |
| Molybdenum | 5–20% |
| Support | Alumina |

The catalyst typically is in the form of extrudates having a diameter of ⅛, 1/16 or 1/32 inches and an L/D of 1.5 to 10. The catalyst also may be in the form of spheres having the same diameters. In their regular form they form too compact a mass and are preferably prepared in the form of a catalytic distillation structure. The catalytic distillation structure must be able to function as catalyst and as mass transfer medium.

Figure 2:
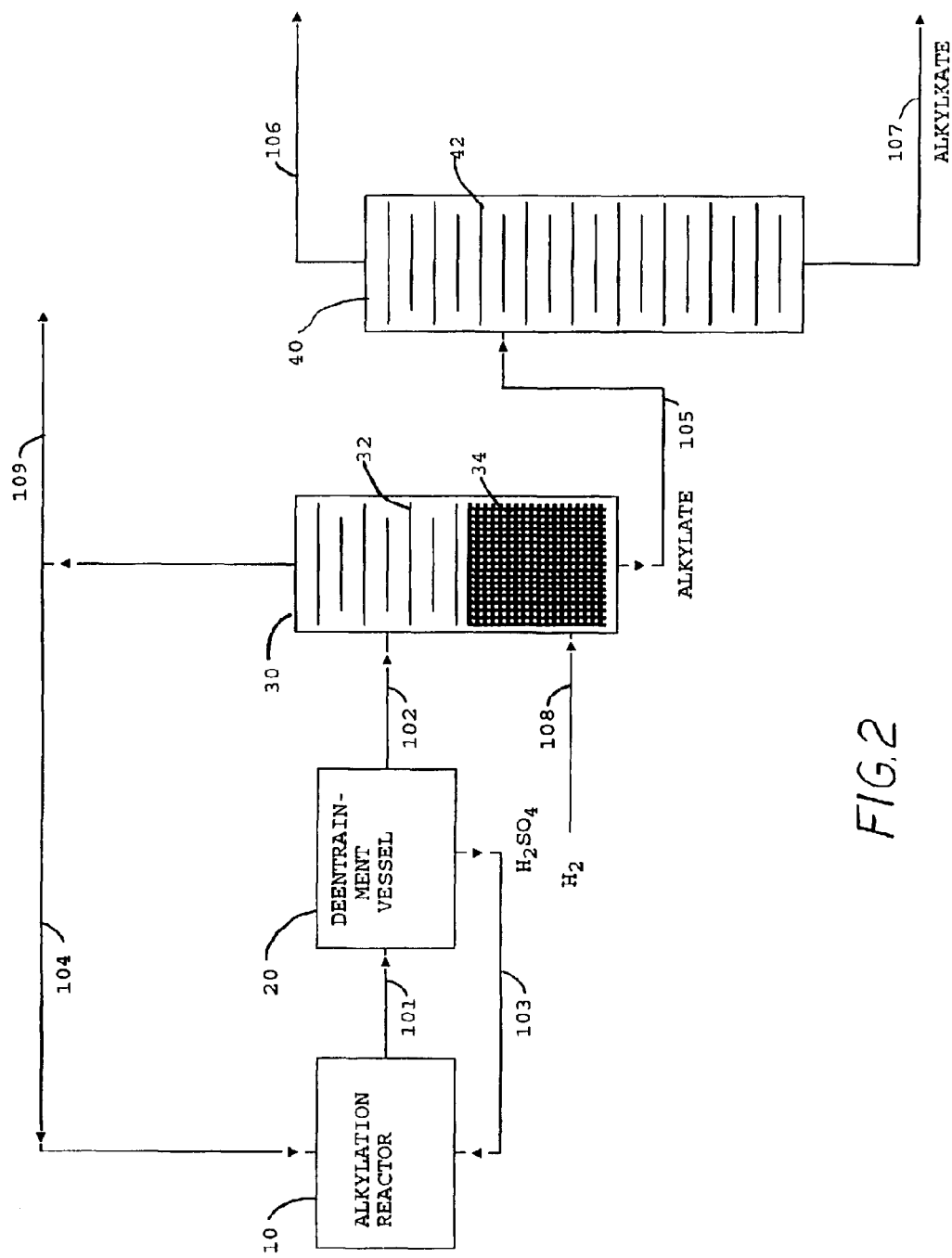
FIG. 2 is a simplified flow diagram in schematic form of a second embodiment of the invention.

A second embodiment is shown in FIG. 2 wherein the hydrodesulfurization catalyst is placed in a bed 34 within the deisobutanizer (DIB). Hydrogen is fed to the deisobutanizer (DIB) via flow line 108. The remainder of the reference numerals are identical to FIG. 1. The hydrogen sulfide is taken in the overheads via flow line 104 along with the isobutane which is recycled to the alkylation reactor 20. Excess hydrogen and trace impurities are removed via flow line 109 or in the embodiment wherein the catalyst bed 34 contains a decomposition catalyst, trace amounts of $SO_2$ and $SO_3$. The metallurgy of the alkylation reactor is capable of handling the corrosive hydrogen sulfide. Although $nC_4$ is shown being removed in a separate tower, it may alternatively be removed as a sidedraw in the DIB tower 30 either above or below the catalyst bed 34. N—$C_4$ is removed in the overheads via flow line 106 along with the normal butane plus trace amounts of $H_2S$ The alkylate product is removed as bottoms via flow line 107.

Figure 3:
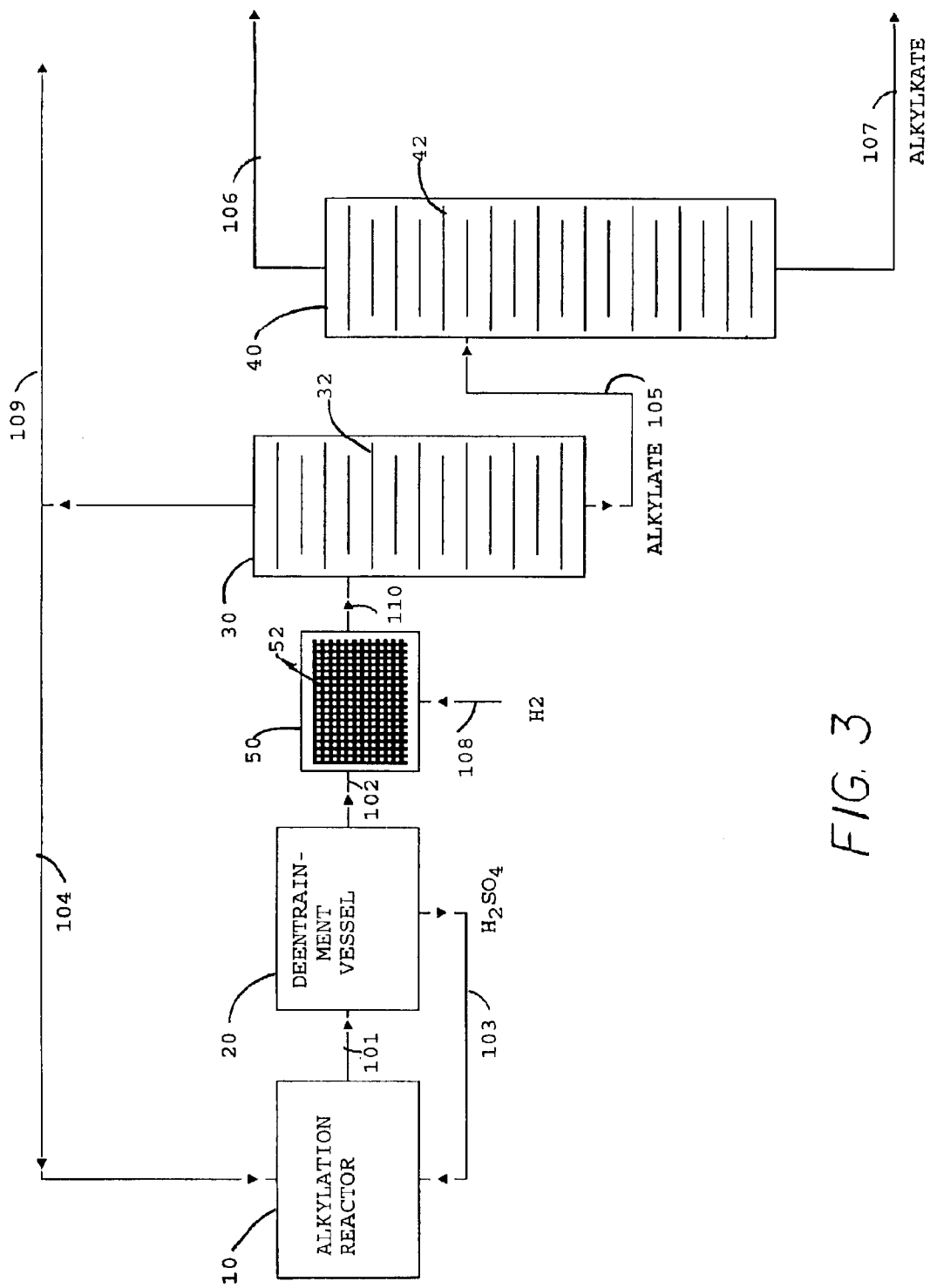
FIG. 3 is a simplified flow diagram in schematic form of a third embodiment of the invention.

A third embodiment is shown in FIG. 3 wherein the hydrodesulfurization catalyst is placed in a bed 52 contained within standard downflow trickle bed reactor 50 immediately following the deentrainment vessel preceding the DIB column. Hydrogen is fed to this reactor via flow line 108. The effluent from the reactor 50 is fed to the DIB column via flow line 110. Again the remainder of the reference numerals are identical to those in FIGS. 1 and 2. The trace amounts of hydrogen sulfide are removed in the overheads from the deisobutanizer (DIB) 30 via flow line 104 along with the isobutane, both being recycled to the alkylation reactor 10. Excess hydrogen and trace impurities are removed via flow line 109 or in the embodiment wherein the catalyst bed 52 contains a decomposition catalyst trace amounts of $SO_2$ and $SO_3$. N—$C_4$ is removed in the overheads via flow line 106 along with the normal butane plus trace amounts of $H_2S$ The alkylate product is removed as bottoms via flow line 107.

In any of the embodiments shown the hydrodesulfurization catalyst may be replaced with a decomposition catalyst such as palladium, which reduces the sulfonates and sulfonic esters to their constituent elements. In this case instead of trace $H_2S$ the sulfur compounds are $SO_2$ and $SO_3$.

The use of the deentrainment vessel with the coalescing material effectively removes the sulfuric acid and removes the necessity of either water wash or caustic treatment of the product from the alkylation reactor.

The invention claimed is:

1. A process for the removal of entrained sulfuric acid and water from the alkylation of olefins with isoalkanes in the presence of sulfuric acid comprising passing the alkylation product through a deentrainment device containing coalescer material to remove the sulfuric acid therefrom and recovering an effluent comprising alkylation product, wherein the effluent from the deentrainment device is contacted with a hydrodesulfurization catalyst to convert any sulfonates and sulfonic esters contained therein to hydrogen sulfide which is removed from the alkylation product.

2. The process according to claim 1 wherein said hydrodesulfurization catalyst is contained within the stripping section of a deisobutanizer (DIB) column which separates isobutane from the alkylation product.

3. The process according to claim 1 wherein said hydrodesulfurization catalyst is contained within the stripping section of a debutanizer column which separates normal butane from alkylation product.

4. A process for the treatment of the effluent from an alkylation reactor wherein a stream containing normal butene is contacted with a stream containing normal and isobutanes in the presence of liquid sulfuric acid under conditions of temperature and pressure to produce isooctane along with sulfonates and sulfonic esters, comprising the steps of:

(a) passing said effluent through a deentrainment device containing coalescer material wherein any entrained sulfuric acid is removed from the effluent;

(b) passing the effluent from said deentrainment device to a deisobutanizer (DIB) column containing a hydrodesulfurization catalyst within the stripping section thereof;

(c) concurrently within said deisobutanizer (DIB) column (i) contacting said sulfonates and sulfonic esters with said hydrodesulfurization catalyst to convert at least a of portion of said sulfonates and said sulfonic esters to hydrogen sulfide;

(ii) separating isobutane and hydrogen sulfide from said effluent as overheads by fractional distillation; and (iii) removing alkylate product and normal butane from said deisobutanizer (DIB) column as bottoms;

(d) recycling the isobutane and hydrogen sulfide to the alkylation process; and (e) separating the normal butane from the alkylate product.

5. The process according to claim 4 wherein the normal butane is separated from the alkylate in a separate debutanizer tower.

6. The process according to claim 4 wherein the normal butane is separated from the alkylate as a side draw in the deisobutanizer (DIB) column.

* * * * *